(12) United States Patent
Gregoriadis et al.

(10) Patent No.: US 6,379,697 B1
(45) Date of Patent: *Apr. 30, 2002

(54) STABILIZATION OF PHOTOSENSITIVE MATERIALS

(75) Inventors: Gregory Gregoriadis, London (GB); Yannis Loukas, Athens (GR)

(73) Assignee: The Secretary of State for Defence in Her Britannic Majesty's Government of the United Kingdom of Great Britain and orthern Ireland, London (GB)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/750,269
(22) PCT Filed: Jun. 1, 1995
(86) PCT No.: PCT/GB95/01258
§ 371 Date: Apr. 9, 1998
§ 102(e) Date: Apr. 9, 1998
(87) PCT Pub. No.: WO95/33448
PCT Pub. Date: Dec. 14, 1995

(30) Foreign Application Priority Data

Jun. 3, 1994 (GB) ............................................. 9411115

(51) Int. Cl.[7] .......................... A61K 9/127; A61K 9/133
(52) U.S. Cl. ......................................... 424/450; 514/58
(58) Field of Search ............................... 424/450, 1.21, 424/9.321, 9.51, 417, 94.3, 812; 514/58; 436/829; 935/54

(56) References Cited

U.S. PATENT DOCUMENTS

| 4,935,407 A | * | 6/1990 | Luider | 514/58 |
| 5,034,228 A | * | 7/1991 | Meybeth | 424/401 |
| 5,811,119 A | * | 9/1998 | Mehta | 424/450 |

FOREIGN PATENT DOCUMENTS

DE 272793 * 10/1989

OTHER PUBLICATIONS

Habib in J. Parentes. Sci. Technol. 45(3) p 124–7, 1991 (Abstract).*
Kirby in Biotechnology. 979–984 1984.*

* cited by examiner

Primary Examiner—Gollamudi S. Kishore
(74) Attorney, Agent, or Firm—Nixon & Vanderhye

(57) ABSTRACT

Liposomes containing a photosensitive material, which undergoes photodegradation on exposure to U.V. light, is retained within the liposome together with a light absorbing material capable of increasing the photostability of the photosensitive. Methods of preparing pharmaceutical compositions containing these liposomes are provided.

28 Claims, 3 Drawing Sheets

STABILIZATION OF PHOTOSENSITIVE MATERIALS

This application is a 371 of PCT/GB95/01258 filed Jun. 1, 1995.

The present invention provides stabilised photosensitive materials and methods for their preparation.

Many drugs and other active agents undergo photodegradation on exposure to UV light and this can be reduced to some extent by combining them with light absorbing agents. Known photostable compounds are capable of acting as light absorbing agents and are used in sunscreens to protect against damage to the skin by radiation, particularly UVA (320–400 nm) and UVB (290–320 nm) radiation, UVB being the most harmful to the skin. Protection is brought about by the absorption of the relevant photons by the chromophore in the sunscreen agent. Alternatively photosensitive materials can be incorporated into cyclodextrins, eg by forming inclusion complexes as described in Andersen F and Bundgarrd H (1984) Int J Pharm 19: pp 189–192.

While such methods are adequate for some purposes improved methods of increasing photostability are desirable, particularly in the area of pharmaceutical medicine where agents must sometimes be administered in their less stable form. In particular a method of increasing photostability would be desirable to lengthen the shelf life of a photosensitive material or its effect when applied locally.

According to this invention a composition comprises a material retained within a liposome, characterised in that the composition further comprises an agent capable of increasing photostabilisation of the composition.

The material to be stabilised by use of the compositions of the present invention is any that may suitably be incorporated into the liposome. This method is particularly useful for the stabilisation of photosensitive materials such as pharmaceuticals or vitamins, eg riboflavin, riboflavin-5'-(dihydrogen-phosphate) or a salt thereof. Organic material, eg organisms may also be photosensitive materials which could be photostabilised by incorporation into liposomes of the present invention.

The liposome may suitably be multilamellar, eg liposomes prepared by the dehydration-rehydration technique, DRVs. These have the advantage of having high yield entrapment values, up to 80% or more. Giant liposomes such as unilamellar giant liposomes capable of entrapping live bacteria may also be utilised in the performance of the present invention. One method of producing such liposomes is described in PCT Patent Application Number WO 95/09610. It is expected that multilamellar liposomes also comprise a number of unilamellar liposomes.

The agent may suitably be associated with the membrane of the liposome, with either the aqueous or lipid phase. Preferred embodiments are those in which the agent is associated with the lipid phase of the membrane but alternatively more than one agent may be included and these may be associated with the same or different phases of the liposome.

The liposomes may be formed from any suitable lipid components, with optional additional components, eg sterols such as cholesterols. Cholesterol enhances the stability of liposomes by inhibiting the movement of acylated chains and increasing the thickness of the bilayers.

According to one aspect of the invention the agent comprises a light absorbing material. The light absorbing material may suitably be any material capable of absorbing some or all visible and/or ultraviolet (UV) light. Preferred light absorbers are those that absorb UV.

Light absorbing materials include chemical absorbers and physical blockers of UV radiation. Chemical absorbers are generally aromatic compounds conjugated with a carbonyl group. In many cases an electron-releasing group (an amine or methoxyl group) is substituted in the ortho- or para- position of the aromatic ring. Chemicals of this configuration absorb the harmful shortwave (high energy) UV rays (250–340 nm) and convert the remaining energy into innocuous longer wave (low energy) radiation (usually above 380 nm). They are excited from their ground state to a higher energy state by the absorption of the UV radiation. As the excited molecule returns to its ground state energy is emitted which is lower in magnitude (longer wavelengths) than the energy initially absorbed to cause the excitation.

Chemical absorbers are characterised not only by their chemical properties but also by their solubility in hydrophobic (oil Red 0, oxybenzone, deoxybenzone) and hydrophilic (sulisobenzone) substances as well. Physical blockers reflect or scatter the ultraviolet, visible and infrared rays and usually include metal oxides. Antioxidants such as beta carotene quench both singlet oxygen driven photochemical reactions and free radical reactions.

Examples of suitable light absorbing materials include azo compounds such as oil Red 0 (solvent red 27; CI26125; 1-[{4-[xylylazo]xylyl}-azo]-2-naphthol), and benzones such as sulisobenzone (5-benzoyl-4-hydroxy-2-methoxy-benzenesulphonic acid), oxybenzone (2-hydroxy-4-methoxy-benzophenone) and deoxybenzone (4-methoxyphenone). Other suitable light absorbing materials will occur to those skilled in the art.

According to another aspect of the present invention the agent comprises a compound capable of forming an inclusion complex with the photosensitive material. Any compound capable of forming a suitable inclusion complex with the photosensitive material may be used. An example of such suitable compounds are the cyclodextrins, these being cyclic oligosaccharides composed of at least six $\alpha 1 \rightarrow 4$ linked D-glucose units with a cavity of fixed size and shape which are capable of forming an inclusion complexes with a variety of materials. The term cyclodextrins will be understood to include cyclodextrins and their derivatives, eg ether, ester and amide derivatives. Suitable cyclodextrins include $\beta$-cyclodextrin, gamma cyclodextrin, hydroxypropyl-cyclodextrin, methyl-$\beta$-cyclodextrin and polymer-$\beta$-cyclodextrin.

One embodiment of the present invention comprises sufficient cyclodextrin to form an inclusion complex comprising $\beta$-cyclodextrin or hydroxypropyl-cyclodextrin in molar ratio photosensitive material:cyclodextrin of 1:1. A further embodiment comprises sufficient cyclodextrin to form an inclusion complex comprising gamma-cyclodextrin, hydroxypropyl-cyclodextrin and polymer-$\beta$-cyclodextrin in molar ratio photosensitive compound:cyclodextrin of 1:2 or 1:1. A still further embodiment comprises polymer-$\beta$-cyclodextrin with molecular weight between 4000 and 4500 as the agent capable of forming an inclusion complex with the photosensitive material.

According to a further aspect of the invention the agent comprises an antioxidant. Suitable antioxidants will be apparent to the person skilled in the art. One such suitable agent is beta-carotene.

It will be understood that the above aspects of the invention are not mutually exclusive. The invention also provides embodiments in which two or more agents are included, selected from light absorbing agents, compounds capable of forming inclusion compounds and antioxidants.

A preferred embodiment of the invention combines the agents described in the first three aspects of the invention in order to express simultaneously and dynamically their protective effect. This may be achieved by using multilamellar vesicles comprising a hydrophilic cyclodextrin capable of forming an inclusion complex with the photosensitive material in the aqueous phase and a combination of light absorbing and antioxidant agents in the lipid bilayer.

The present invention also provides methods of producing a composition as described above comprising the incorporation into a liposome of an agent capable of effecting the photostabilisation of the composition; in particular methods wherein the liposome is prepared by a dehydration rehydration technique.

One embodiment of this aspect of the invention provides a method comprising:

(a) mixing the components from which the liposome is to be formed in the presence of an organic solvent;

(b) evaporating the solvent;

(c) dispersing the film formed in (b) in water and isolating the liposomes so produced, characterised in that an agent capable of effecting photostabilisation is added in step (a) and/or (c) and the photosensitive material is added in step (c) or on further rehydration after dehydration.

Any suitable organic solvent may be used in step (a), eg chloroform. In step (b) the solvent may suitably be evaporated by rotary evaporation. Dispersion in step (c) may be performed by any suitable method, a preferred method being sonication, using an ultrasonic probe.

The agent capable of effecting photostabilisation may be added in step (a) if lipid soluble or in step (c) if aqueous soluble. The photosensitive material is added in step (c) or on rehydration after further dehydration. The photosensitive material may be added in aqueous solution or it may be added in the form of an inclusion complex.

The liposomes formed may be freeze dried and the resulting pellets or powder stored until further required when they can be rehydrated.

The present invention further provides pharmaceutical mixtures comprising a composition as described above together with a physiologically acceptable carrier, suitable for administering to a living organism preferably compositions suitable for administering to humans. Furthermore the invention provides pharmaceutical mixtures comprising a composition as described above together with a physiologically acceptable carrier characterised in that it is suitable for administration to a human by injection, orally, inhalation or topical administration.

Suitable physiologically acceptable carriers to be included in such compositions will occur to those skilled in the art, eg saline solutions.

The materials and methods of the invention will now be illustrated by example only with reference to the following non-limiting examples. Further embodiments will occur to those skilled in the art in the light of these.

EXAMPLE 1

PREPARATION OF STABILISED PHOTOSENSITIVE MATERIALS

Figure 1:
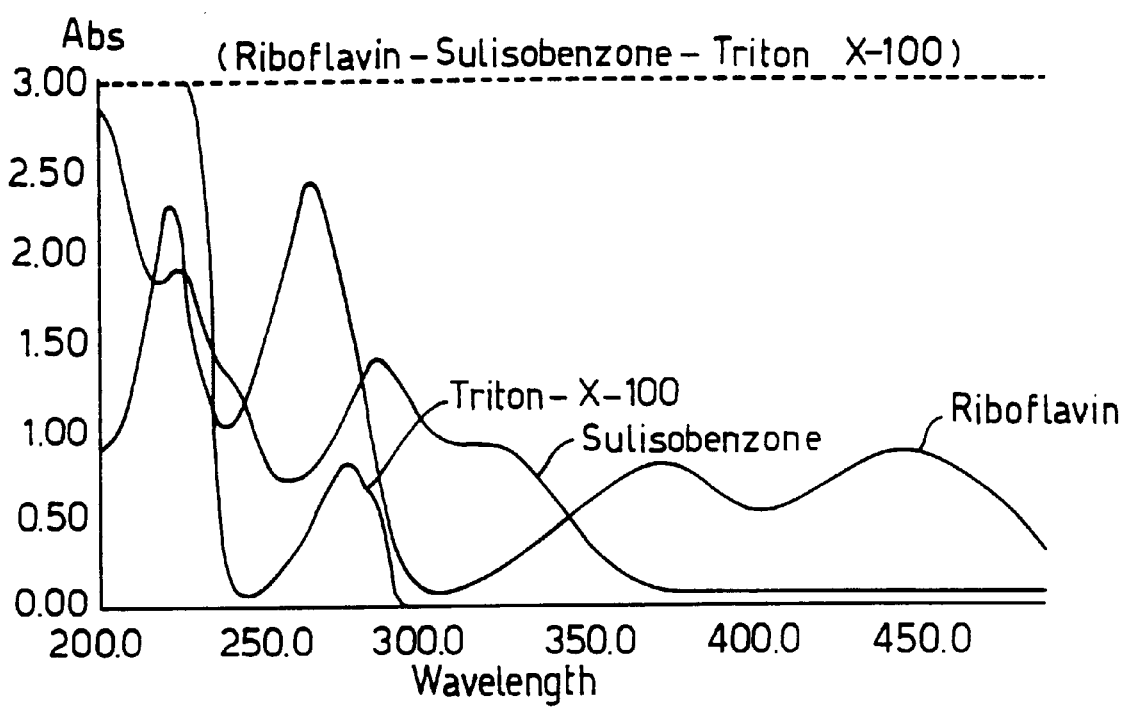
FIG. 1 shows UV spectra of riboflavin. Triton-X-100 (RTM) and sulisobenzone in doubly distilled water.

In order to study the efficiency of photostabilising methods the present inventors have used Vitamin $B_2$ (riboflavin) as a model light sensitive compound. Although in its dry form riboflavin is not affected by visible or ultraviolet light, irradiation causes it to rapidly decompose in aqueous solutions with the subsequent formation of lumichrome and/or lumiflavin. This occurs at a rate of $2.4 \times 10^{-2}$ $min^{-1}$, the compound having a half life of about 30 mins. Riboflavin has maximum absorptions in UV and visible range of 222, 266, 373 and 444 nm as shown in FIG. 1 and when it degrades there is a resultant decrease in absorbance at 444 nm which provides a suitable point at which to study its photodegradation. In these particular experiments the inventors have used the sodium salt of riboflavin phosphate as a suitable model light sensitive agent.

Equimolar egg phosphatidylcholine (PC) and cholesterol (both obtained from Sigma Chemicals Company) were dissolved in analytical grade chloroform in a spherical flask. The chloroform was evaporated under rotary evaporation at 30° C. and 60 rpm in order to form a lipid film. 5 ml double distilled water was added and the mixture vortexed with glass beads to resuspend the lipid film in the aqueous phase giving an homogenous suspension which was then flushed with oxygen free nitrogen to remove traces of oxygen which could oxidise the lipid.

The suspension was probe sonicated 15 times at 4° C., each time for one minute with 30 second intervals. The sonicated suspension containing small unilamellar vesicles (SUV) was centrifuged at 4000 rpm for ten minutes to isolate contaminating titanium fragments derived from the sonicator probe which were discarded. 5 ml of an aqueous solution of riboflavin was added and the resulting suspension flushed with nitrogen before being freeze dried overnight. It was then rehydrated with 0.1 ml double distilled water followed by 0.1 ml PBS buffer and allowed to stand for at least an hour at 20° C. in order to complete the rehydration.

0.8 ml PBS was added and the resulting mixture centrifuged at 20000 rpm and 4° C. to remove any untrapped materials. This was repeated twice and all three supernatants pooled. The isolated pellets were then resuspended in 0.8 ml PBS and the percentage of entrapment calculated by UV or fluorescence.

The above procedure was repeated incorporating light absorbing agents into the liposomes. Liposomes containing the lipid soluble oil Red 0 were prepared by mixing oil Red 0 (obtained from Sigma Chemicals) with the phosphatidyl choline and cholesterol at the start of the procedure. Liposomes containing an aqueous soluble light absorbing agent sulisobenzone were prepared by adding sulisobenzone (also obtained from Sigma Chemicals) at the same time as the riboflavin-5'-dihydrogen phosphate monosodium salt (obtained from Aldrich Chemical Company). Further liposomes were prepared comprising both these agents together with the riboflavin. The different preparations produced are shown below in Table 1.

TABLE 1

DRV LIPOSOMES CONTAINING RIBOFLAVIN
AND LIGHT ABSORBING AGENTS

| DRV Formln | Egg PC (mg) | Cholesterol (mg) | Riboflavin (mg) | Oil Red 0 (mg) | Sulisobenzone (mg) |
|---|---|---|---|---|---|
| 1 | 10 | 5 | 0.66 | — | — |
| 2 | 10 | 5 | 0.66 | 0.72 | — |
| 3 | 10 | 5 | 0.66 | — | 0.75 |
| 4 | 10 | 5 | 0.66 | 0.72 | 0.75 |

The entrapment of riboflavin and light absorbing agents in liposomes was calculated by UV or fluorescence. A known amount of liposome suspension was dissolved in Triton-X-100 (RTM) (obtained from Sigma Chemicals) at 70° C., a known amount of distilled water added and the absorbance (A) of riboflavin or light absorbing agent measured. The absorbance of the three supernatants ($A^1$, $A^2$ and $A^3$) was also measured. Entrapment was then calculated as follows:

% entrapment=$A/A_{total} \times 100$, where $A_{total}=A+A^1+A^2+A^3$

The percentage entrapment of riboflavin and light absorbing agents in all preparations and the wavelength used for each is shown below in Table 2.

TABLE 2

PERCENTAGE ENTRAPMENT OF THE COMPOUNDS
USED IN DRV LIPOSOMES

| DRV Formln | Riboflavin | Oil Red 0 | Sulisobenzone |
|---|---|---|---|
| 1 | 45 (444 nm) | — | — |
| 2 | 39 (fluorometrically) | 95 (520 nm) | — |
| 3 | 40 (444 nm) | — | 50 (319 nm) |
| 4 | 45 (fluorometrically) | 90 (520 nm) | 40 (319 nm) |

All entrapment values denote percentage of the amount used.

EXAMPLE 2

PREPARATION OF CYCLODEXTRIN INCLUSION COMPLEXES

An aqueous solution of riboflavin (24 mg/ml) was divided into five portions and a cyclodextrin or derivative (both obtained from Wacker Chemie) added dropwise to each. Betacyclodextrin was added to the first portion and hydroxy-β-cyclodextrin to the second, each providing a molar ratio (drug:cyclodextrin) of 1:1. Hydroxypropyl-cyclodextrin was added to the third portion, methyl-β-cyclodextrin to the fourth and polymer β-cyclodextrin (average molecular weight 4000–4500) to the last; each to provide a molar ratio (drug:cyclodextrin) of 1:2. The resulting solutions were stirred in the dark at room temperature for two days after which time the clear yellow solutions obtained were frozen at −40° C. and freeze dried overnight.

EXAMPLE 3

EXPOSURE OF THE PREPARATIONS PRODUCED ACCORDING TO THE METHODS OF EXAMPLES 1 AND 2 TO UV IRRADIATION

The preparations produced according to the methods of Examples 1 and 2 were exposed to UV irradiation as follows: 3 ml of the solutions, liposome suspensions or complexes in solution were placed in a 1×1×4 $cm^3$ cuvette cell (1 cm path length) and irradiated from the sided at a fixed distance of 3 cm with a UV lamp (254/365 nm) at 24° C.+/−1. At time intervals a known amount of the solution or suspension was diluted with double distilled water and the absorbance or fluorescence measured.

In the case of the liposome suspensions liposomal pellets were produced, solubilised with a 10% solution of Triton-X-100 (RTM) and then diluted and measured. The spectra of Triton-X-100 (RTM), riboflavin and sulisobenzone are shown in FIG. 1. The entrapment and degradation of riboflavin was calculated from the absorbance readings at 444 nm, absorbance at this wavelength not interfering with the absorbance of Triton-X-100. When oil Red 0 was present in the liposomes the fluorescence of riboflavin was used for each estimation (excitation and emission wavelengths 445 and 520 nm respectively).

The photodegradation of riboflavin caused by UV irradiation follows first order kinetics and is given by the following equation:
Equation 1

$$C=C_0 e^{-kt} \tag{1}$$

where $C_0$ is the initial concentration of riboflavin, C is the concentration of riboflavin after t min of irradiation and k is the first order photodegradation rate constant.

Equation (1) is in the exponential form and can be transformed logarithmically to the linear form,
Equation 2

$$\ln C = \ln C_0 - kt \tag{2}$$

The graphic representation of Equation (2) is linear and the slope of the line gives the photodegradation rate constant k. In all experiments k was calculated according to a linear least-square regression analysis of equation (2). k is independent of the initial concentration of R as can be shown by the degradation lines of solutions containing increasing concentrations of riboflavin. All the lines have the same slope. From the various rate constants k the corresponding half lives ($t_{50}$%) of riboflavin in front of UV light can be calculated in all preparations, according to the formula $t_{50\%}=0.693/k$, which characterises first order kinetics.

The increase in stability was expressed by the stabilization ratio. ($k_0/k$), where $k_0$ is the photodegradation constant of free riboflavin in aqueous solution and k the photodegradation rate constant of the various preparations.

In cases where oil Red 0 was included in the liposome preparation. an apparent reduction in the absorbance of riboflavin was caused which was avoided by using fluorescence to calculate riboflavin entrapment. The photodegradation rate constant k in all preparations, the increase in stability ($k_0/k$) and the correlation coefficient are all shown in Table 3 below.

TABLE 3

RATE CONSTANTS FOR THE PHOTODEGRADATION OF
RIBOFLAVIN IN DIFFERENT FORMULATIONS:
DEMONSTRATING THE INCREASE IN STABILITY

|  | k × $10^3$ ($min^{-1}$) | r | $k_0/k$ |
|---|---|---|---|
| Riboflavin | 24($k_0$) | 0.99 |  |
| DRV-1 | 18 | 0.98 | 1.3 |

TABLE 3-continued

RATE CONSTANTS FOR THE PHOTODEGRADATION OF RIBOFLAVIN IN DIFFERENT FORMULATIONS: DEMONSTRATING THE INCREASE IN STABILITY

|  | k × 10³ (min⁻¹) | r | $k_0/k$ |
|---|---|---|---|
| DRV-2 | 0.37 | 0.99 | 65 |
| DRV-3 | 5.33 | 0.98 | 4.5 |
| DRV-4 | 0.42 | 0.99 | 57.2 |
| Riboflavin + oil Red * | 10 | 0.97 | 2.4 |
| Riboflavin + Sulisobenzone** | 14 | 0.98 | 1.7 |
| Riboflavin: betacyclodextrin 1:1 | 8 | 0.99 | 3 |
| Riboflavin: hydroxypropylbetacyclodextrin 1:1 | 4 | 0.99 | 4 |
| Riboflavin: hydroxypropylbetacyclodextrin 1:2 | 12 | 0.97 | 2 |
| Riboflavin: gammacyclodextrin 1:2 | 10 | 0.97 | 2.4 |
| Riboflavin: polymer-β-cyclodextrin 1:2 | 14 | 0.99 | 1.7 |

*Aqueous solution containing riboflavin and Red Oil 0 (solubilised in Triton-X-100 (RTM))
**Aqueous solution containing riboflavin and sulisobenzone From the results shown in Table 3 above it can be concluded that riboflavin is photodegraded at a much slower rate (65 fold reduction in degradation rate) when the vitamin is co-entrapped with oil Red 0 in liposomes. These results, in conjunction with the high loading capacity of DRV for both riboflavin and light absorbing agents, suggests that DRV liposomes incorporating oil Red 0 could serve effectively for the protection of coentrapped photosensitive agents.

EXAMPLE 4

CO-ENTRAPMENT OF CYCLODEXTRIN INCLUSION COMPLEXES OF RIBOFLAVIN TOGETHER WITH LIGHT ABSORBING AGENTS IN LIPOSOMES

Riboflavin gamma-cyclodextrin inclusion complexes were entrapped in DRV incorporating a light absorbing agent or antioxidant in their lipid phase selected from: oil Red 0, oxybenzone, deoxybenzone and beta-carotene or combinations thereof. The resulting liposomes were exposed to UV light (254/365 nm) and their photodegradation at different time intervals monitored spectrophotometrically (excitation 445 nm, emission 520 nm). As in the previous examples this degradation followed first order kinetics represented by the equations given earlier.

Figure 2:
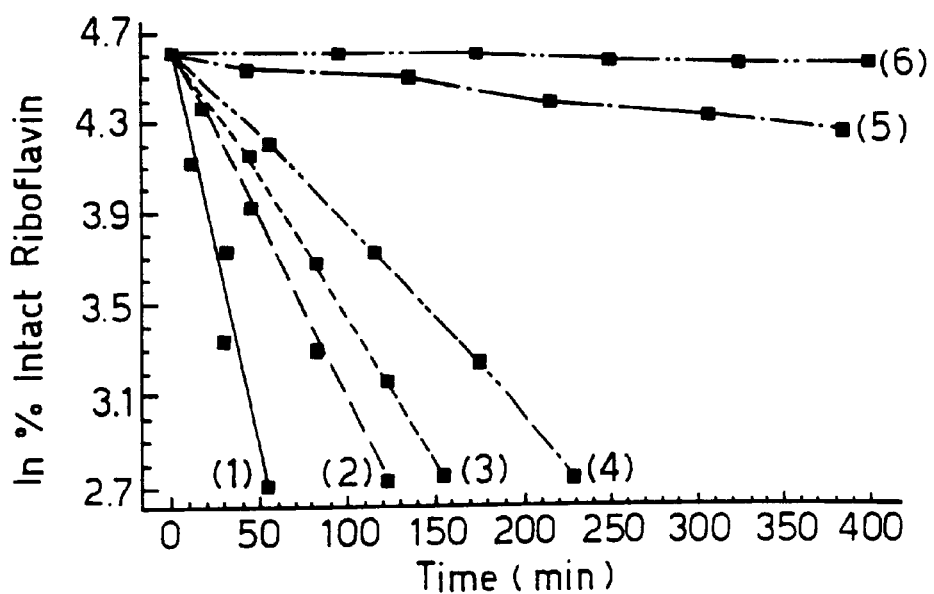
FIG. 2 shows the photodegradation kinetics of the preparations of examples 1, 2 and 4.

The results obtained, shown graphically in FIG. 2, indicate that the photostability of riboflavin entrapped alone in DRV increases 4-fold (line 2) compared to that for free riboflavin in water (line 1). A modest increase in photostability (to 6-fold) is also obtained with riboflavin-gamma-cyclodextrin inclusion complex in water (line 3). Stability is increased 20-fold when riboflavin-gamma-cyclodextrin inclusion complex is entrapped in DRV (line 4) and 210-fold when co-entrapped in DRV with oil Red 0, oxybenzone and deoxybenzone (line 5). Stability values reach a maximum (260-fold increase) when the anti-oxidant beta-carotene is included in the liposomes containing the riboflavin-gamma-cyclodextrin inclusion complex and the light absorbing agents (line 6).

EXAMPLE 5

PREPARATION OF RIBOFLAVIN CONTAINING LIPOSOMES

The method of Example 1 was repeated with a few alterations. The freeze dried material was rehydrated in 1 ml of double distilled water rather than 0.1 ml by vortexing, with the resulting suspension then being allowed to stand for 30 minutes at room temperature after which 1 ml of PBS was added followed by a further 6 ml PBS. The suspension was centrifuged at 20,000 rpm at 4° C. to remove any untrapped material and this process repeated three times and the three supernatants collected. The resulting pellets were stored and later resuspended and used in the photodegradation study of Example 7.

In order to provide multilammelar vesicles (MLV) this method was repeated but with the variation that once formed the lipid film was dispersed using PBS containing the solutes to be entrapped, ie free or complexed riboflavin. The resulting suspension was allowed to stand for 2 hours at room temperature in order to allow the swelling process to complete and the suspension was then centrifuged as described above in order to isolate pellets. Table 4 shows the composition of the resulting preparations.

TABLE 4

LIPOSOME PREPARATIONS OF FREE RIBOFLAVINS

| No. | Egg PC | Cholesterol | Riboflavin | oil Red 0 | Oxybenzone | Deoxybenzone | Sulisobenzone |
|---|---|---|---|---|---|---|---|
| DRV 1 | 0.04 | 0.04 | 0.004 | | | | |
| DRV 2 | 0.04 | 0.04 | 0.004 | 0.008 | | | |
| DRV 3 | 0.04 | 0.04 | 0.004 | | 0.004 | 0.004 | |
| DRV 4 | 0.04 | 0.04 | 0.004 | 0.004 | 0.002 | 0.002 | |
| DRV 5 | 0.04 | 0.04 | 0.004 | 0.004 | 0.002 | 0.002 | 0.004 |
| MLV 1 | 0.04 | 0.04 | 0.004 | | | | |
| MLV 2 | 0.04 | 0.04 | 0.004 | 0.008 | | | |

All values are expressed in mmol.

Further liposomes were produced and their compositions are shown below in Table 5.

TABLE 5

LIPOSOME PREPARATIONS OF FREE RIBOFLAVIN

| No. | Egg PC | Cholesterol | Riboflavin | oil Red 0 | Oxybenzone | Deoxybenzone | Sulisobenzone |
|---|---|---|---|---|---|---|---|
| DRV1 a | 0.04 | 0.04 | 0.004 | | | | |
| DRV2 a | 0.04 | 0.04 | 0.004 | 0.008 | | | |
| DRV3 a | 0.04 | 0.04 | 0.004 | | 0.008 | | |
| DRV4 a | 0.04 | 0.04 | 0.004 | | | 0.008 | |
| DRV5 a | 0.04 | 0.04 | 0.004 | | | | 0.004 |

All values are expressed in mmol.

EXAMPLE 6

PREPARATION OF CYCLODEXTRIN COMPLEXES

Equimolar quantities of riboflavin and either β-cyclodextrin or gamma-cyclodextrin were dissolved in double distilled water. The clear aqueous solution of riboflavin was then added dropwise to each of these cyclodextrin solutions while they were stirred and the resulting solution was left in the dark at room temperature for 2 days with continuous stirring. The resulting yellow solution was then frozen at −40° C. and freeze dried overnight to yield an amorphous yellow powder. Table 6 below shows the composition of the resulting preparations.

The organic phases were combined and the final solution measured by UV spectroscopy using the characteristic lambda-max of each compound. The concentration of unentrapped light absorber was calculated from calibration curves. The aqueous phase was measured fluorometrically to determine the unentrapped riboflavin then frozen and freeze dried overnight. The stoichometry of the solid materials containing riboflavin complexes was measured by $^1$H NMR in $D_2O$. Digital integration of selected NMR signals form riboflavin and cyclodextrins provided direct access to the stoichometry coefficient enabling the amount of unentrapped cyclodextrin to be determined. The entrapment values of riboflavin and of the other materials were calculated by subtracting the untrapped material from initial total concentration, according to the following expression:

TABLE 6

LIPOSOME PREPARATIONS OF COMPLEXED RIBOFLAVIN

| No. | Egg PC | Cholesterol | R:beta CD | R:γ CD | oil Red 0 | Oxybenzone | Deoxybenzone | Sulisobenzone |
|---|---|---|---|---|---|---|---|---|
| DRV6 | 0.04 | 0.04 | 0.004 | | | | | |
| DRV7 | 0.04 | 0.04 | | | 0.004 | | | |
| DRV8 | 0.04 | 0.04 | 0.004 | | 0.008 | | | |
| DRV9 | 0.04 | 0.04 | | 0.004 | 0.008 | | | |
| DRV1 10 | 0.04 | 0.04 | 0.004 | | 0.004 | 0.002 | 0.002 | |
| DRV1 11 | 0.04 | 0.04 | | 0.004 | 0.004 | 0.002 | 0.002 | |
| DRV1 12 | 0.04 | 0.04 | | 0.004 | 0.004 | 0.0015 | 0.0015 | 0.0015 |
| MLV 3 | 0.04 | 0.04 | 0.004 | | | | | |

EXAMPLE 7

STUDIES ON THE PREPARATIONS OF EXAMPLES 5 AND 6

Entrapment values of the liposomal preparations formed by the methods of Examples 5 to 7 were determined as follows: entrapment values for liposome preparations comprising light absorbers were determined by derivative ultraviolet spectroscopy; for riboflavin by fluorescence and for cyclodextrins (complexed riboflavin) by $^1$H NMR in $D_2O$.

After centrifugation and isolation of the liposomal pellets the three supernatants were combined and extracted twice with chloroform in order to separate the hydrophobic light absorbers and the hydrophilic riboflavin free or complexed.

$$\% \text{ entrapment} = \frac{A_0 - A}{A_0} 100$$

where $A_0$ is the absorbance or fluorescence of the initial concentration of each material and A is the absorbance or fluorescence of the untrapped material (corresponding to the combined supernatants) after the dilution correction (so as $A_0$ and A have the same dilution).

This method of calculating entrapment has the advantage that it separates the hydrophobic from the hydrophilic materials. The entrapment of riboflavin was first calculated in the aqueous phase fluorimetrically. The resulting values were confirmed by measuring the entrapped riboflavin in liposomal pellets directly, after dilution with Triton-X-100, both values were the same with a deviation of ±2%.

After the entrapment of riboflavin was calculated the molar ratio R:CD in the aqueous phase was measured by integrating the anomeric protons of CDs (H1 protons. 7 in β-cyclodextrin, 8 and gamma-cyclodextrin) with the phenyl protons of riboflavin (two protons). In all preparations the 1:1 molar ratio in the aqueous phase indicated that the riboflavin was entrapped in liposomes as a 1:1 complex. If the molar ratio of the complexes riboflavin:cyclodextrin was not 1:1, possible interaction in the liposomes would be expected.

After this procedure the chloroformic organic phase was measured spectrophotometrically to determine the untrapped lipid light absorbers. In all preparations the entrapment values for the lipid soluble light absorbers and the beta carotene were 93–98%. Only when cholesterol was absent were the entrapment values much lower (around 50%).

The preparations of Examples 5 and 6 were exposed to UV light as described in Example 3 and their photodegradation studied.

Figure 3:
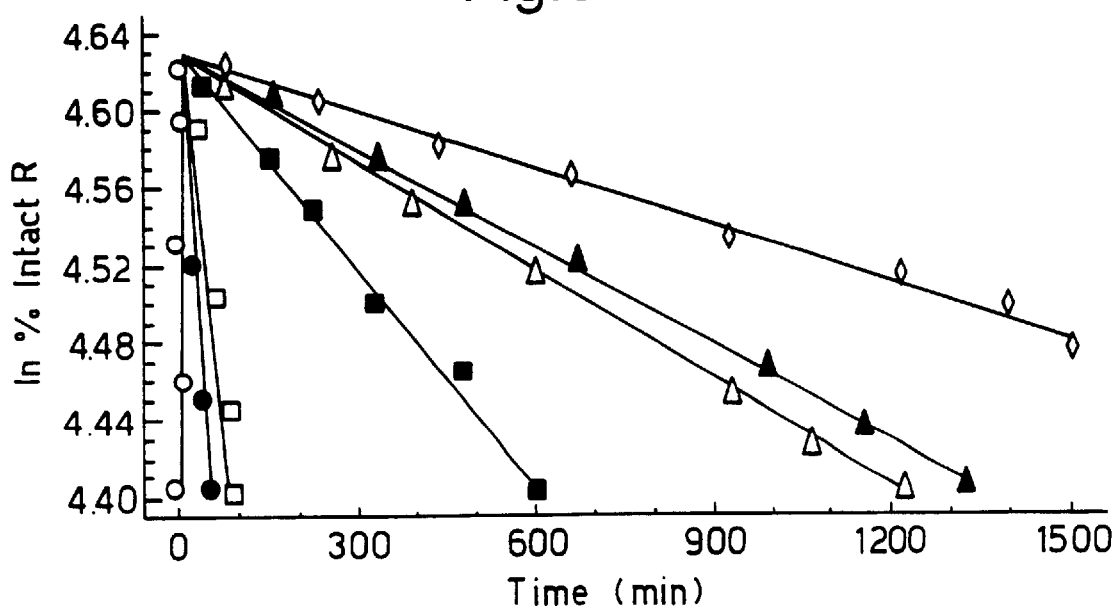
FIG. 3 shows the photodegradation kinetics of the preparations of examples 5 and 6.

Tables 7 and 8 below show the percentage of entrapment in the preparations of Examples 5 to 6, together with their photodegradation rate constants, stabilization ratios and correlation coefficients r of the kinetic studies. The results are illustrated in FIG. 3, wherein (0) denotes free riboflavin, (•) free riboflavin in DRV, (□) 1:1 riboflavin:gamma-cyclodextrin complex, (■) free riboflavin co-entrapped in DRV with oil Red 0, (Δ) riboflavin:gamma-cyclodextrin complex, co-entrapped in DRV with oil Red 0, (▼) riboflavin:gamma-cyclodextrin complex, co-entrapped in DRV with oil Red 0, oxybenzone and deoxybenzone, (☆) riboflavin:gamma-cyclodextrin complex, co-entrapped in DRV with oil Red 0, oxybenzone, deoxybenzone and β-carotene.

TABLE 7

CHARACTERISTICS OF DIFFERENT LIPOSOMB PREPARATIONS

| No | % entrapment of R | $k_L \times 10^4$ (min$^{-1}$)[a] | Stabilisation Ratio | r |
|---|---|---|---|---|
| DRV1 | 47 | 60 | 4 | 0.991 |
| DRV2 | 43 | 3.7 | 65 | 0.982 |
| DRV3 | 44 | 22 | 11 | 0.983 |
| DRV4 | 44 | 3.2 | 75 | 0.981 |
| DRV5 | 27 | 3.4 | 70 | 0.976 |
| DRV6 | 23 | 20 | 12 | 0.991 |
| DRV7 | 20 | 12 | 20 | 0.992 |
| DRV8 | 21 | 1.9 | 126 | 0.978 |
| DRV9 | 19 | 1.4 | 171 | 0.975 |
| DRV10 | 21 | 1.58 | 152 | 0.973 |
| DRV11 | 20 | 1.14 | 210 | 0.989 |
| DRV12 | 19 | 0.92 | 260 | 0.983 |
| DRV12a | 10 | 1.1 | 218 | 0.973 |
| DRV12b | 16 | 1 | 240 | 0.966 |
| DRV12c | 18 | 0.92 | 260 | 0.968 |
| DRV12d | 20 | 1.5 | 160 | 0.979 |
| DRV12e | 8 | 1.1 | 218 | 0.983 |
| DRV12f | 12 | 1 | 240 | — |
| MLV1 | 5 | 160 | 1.5 | 0.976 |
| MLV2 | 3.5 | 24 | 10 | 0.969 |
| MLV3 | 1.5 | 80 | 3 | 0.984 |

[a]$k_0 \times 10^4$ is equal to 240.

TABLE 8

CHARACTERTICS OF FURTHER LIPOSOME PREPARATIONS

| No | % entrapment of R | $k_L \times 10^4$ (min$^{-1}$)[a] | Stabilisation Ratio ($K_0/K_L$) | r |
|---|---|---|---|---|
| DRV1a | 47 | 60 | 4 | 0.991 |
| DRV2a | 43 | 3.7 | 65 | 0.982 |
| DRV3a | 41 | 34 | 7 | 0.986 |
| DRV4a | 42 | 48 | 5 | 0.975 |
| DRV5a | 26 | 48 | 5 | 0.988 |

From these results it can be concluded that no correlation exists between the entrapment values or the stabilisation ratios of MLV liposomes and DRV liposomes prepared using the same quantities of materials. The low values for entrapment of the vitamin in the MLV liposomes can be explained by the fact that the adjacent bilayers are stacked very closely to one another with very little aqueous space between them. Because the bilayer sheets were sealed into the vesicles before the complete hydration of the lipid headgroups, liposomes were formed with an uneven distribution of solute throughout the bilayers. By contrast the formation of the DRV liposomes involving the dehydration/rehydration cycle results in vesicles being formed which are more concentrated and are in close contact with solute resulting in the formation of liposomes with greater entrapment and more stable lamellarity. This was verified by the observation of a decreased rate of loss of entrapped riboflavin when the liposomes were suspended in PBS.

The photodegradation kinetic studies of riboflavin were performed in the formulations prepared by the methods of Examples 5 and 6 by monitoring the reduction of riboflavin's fluorescence with time. In the presence of Triton-X-100 negligible change in the fluorescence of riboflavin was observed. The addition of oil Red 0 caused an apparent reduction in the fluorescence of riboflavin. In order to determine the extent of this reduction and to determine whether during the photodegradation of riboflavin the same concentration of oil Red 0 caused different reductions in fluorescence, solutions containing known amounts of riboflavin and oil Red 0 solubilised in water using Triton-X-100 were prepared and their fluorescence measured. These results are shown below in Table 9. From these results the reduction factor (r.f.) can be calculated as follows:

$$r.f = F_{(+)}/F_{(-)}$$

where $F_{(+)}$ is the fluorescence of riboflavin in the presence of oil Red 0 and $F_{(-)}$ is the fluorescence of riboflavin in the absence of oil Red 0.

TABLE 9

REDUCTION OF RIBOFLAVIN FLUORESCENCE IN SOLUTIONS IN THE PRESENCE OF OIL RED 0

| Riboflavin (μg/ml) | Oil Red 0 (μg/ml) | fluorescence | r.f. |
|---|---|---|---|
| 1.23 |  | 280.9 | 1 |
| 1.65 |  | 368.9 | 1 |
| 2.06 |  | 433.3 | 1 |
| 1.23 | 9 | 249.6 | 0.89 |
| 1.65 | 9 | 324.6 | 0.88 |
| 2.06 | 9 | 381.3 | 0.88 |
| 1.23 | 18 | 212.1 | 0.75 |

TABLE 9-continued

REDUCTION OF RIBOFLAVIN FLUORESCENCE IN SOLUTIONS IN THE PRESENCE OF OIL RED 0

| Riboflavin ($\mu$g/ml) | Oil Red 0 ($\mu$g/ml) | fluorescence | r.f. |
|---|---|---|---|
| 1.65 | 18 | 272.9 | 0.74 |
| 2.06 | 18 | 320.6 | 0.74 |

Figure 4:
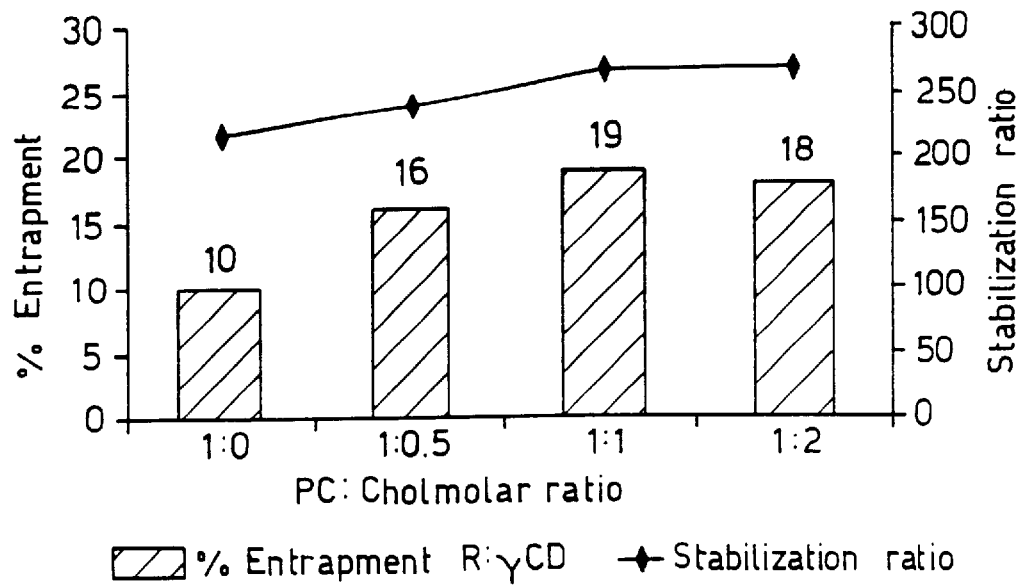
FIG. 4 shows the percentage entrapments and stabilisation ratios of liposomes comprising different ratios of phosphatidylcholine and cholesterol.
Figure 5:
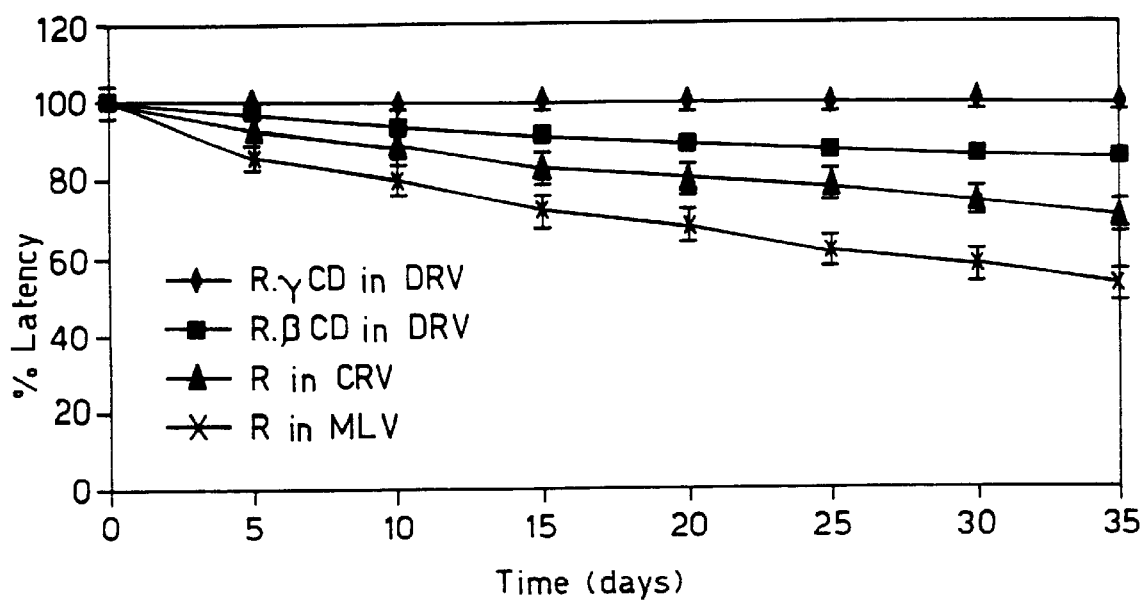
FIG. 5 shows the latency (% retention of riboflavin) values of various liposome preparations.
Figure 6:
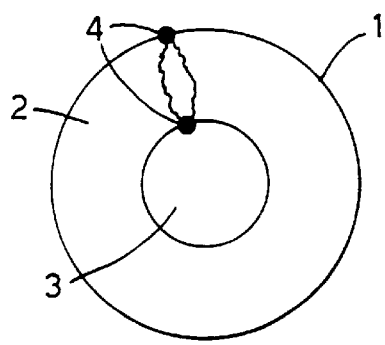
FIG. 6 shows a diagrammatic representation of the present invention.

From the values of r.f. it was established that r.f. is a constant dependent on the concentration of the oil Red 0 but not on the concentration of riboflavin. From a comparison of the concentration of the transmissions of the oil Red 0 solutions with the r.f. values as shown in Table 10, it was determined that $$r.f. = T_{445} \times T_{520}$$

where $T_{445}$ and $T_{520}$ are the transmissions of the oil Red 0 solutions at 445 and 520 nm respectively. This suggests that the reduction in fluorescence is due to the absorbance of $(1-T_{455}) \times 100\%$ of the excited light and of $(1-T_{520}) \times 100\%$ of the light emitted by oil Red 0. Using these equations the concentration of riboflavin was determined even in the presence of oil Red 0. It was concluded that oil Red 0 did not interfere during the kinetic studies and its effect was cancelled out. The results for the various preparations are shown in FIGS. 4 and 5.

TABLE 10

TRANSMISSIONS OF OIL RED 0 SOLUTIONS AS DETERMINED BY UV SPECTROPHOTOMETRY

| Oil Red 0 ($\mu$g/ml) | $T_{445}$ | $T_{520}$ | $T_{445} \times T_{450}$ |
|---|---|---|---|
| 9 | 0.941 | 0.947 | 0.89 |
| 18 | 0.864 | 0.849 | 0.73 |

EXAMPLE 8

STUDYING THE EFFECT OF VARYING THE COMPOSITION AND THE METHOD OF PRODUCING THE LIPOSOME

The lipids used and the presence of cholesterol in the liposome preparations was found to affect the entrapment values and the stabilisation ratios. Distearoyl-phosphatidylcholine (DSPC, obtained from Sigma Chemicals) was incorporated into the liposomes by following the same procedure as detailed in Example 1 at 60° C. Lower entrapment values for riboflavin were achieved and a substantial decrease in stabilisation ratio observed in the absence of cholesterol, as shown below in Table 11. This is also illustrated in FIG. 4.

Cholesterol enhances the stability of liposomes by inhibiting the movement of acylated chains and increasing the thickness of the bilayers. Above the transition temperature (except when DSPC is present) cholesterol diminishes fluidity resulting in a considerable reduction in riboflavin release, increasing the stabilisation ratio. Increasing the amount of cholesterol to 1:1 (phospholipid:cholesterol) increased the entrapment value with a simultaneous increase in stabilistion. Molar ratio of phosphatidyl choline:cholesterol of 1:2 had no effect on the entrapment values or the stabilisation ratio. Substitution of the unsaturated lipid PC with saturated DSPC in the DRV preparations did not increase the stabilisation ratio. The light absorbing compounds appear to be responsible for the protection of the riboflavin and also for the prevention of UV driven oxidation of the lipids.

In order to optimise the photostabilisation variations were made to the method of liposome preparation, the variations are shown below in Table 11.

TABLE 11

VARIATION OF LIPOSOME PREPARATION PROCEDURE

| No | PC | Chol | DSPC | Type of Variation |
|---|---|---|---|---|
| DRV12a | 0.04 | — | 13 | liposomes without cholesterol |
| DRV12b | 0.04 | 0.02 | | molar ratio PC:Chol 1:0.5 |
| DRV12c | 0.04 | 0.08 | | molar ratio PC:Chol 1:2 |
| DRV12d | | 0.04 | 0.04 | substitution of PC with DSPC |
| DRV12e | | | | addition of R:gamma-CD aqueous solution during the rehydration procedure |
| DRV12f | | | | Omission of the sonication step in DRV preparation |

DRV liposomes were prepared by adding an aqueous solution of vitamin before the freeze drying step, further DRV liposomes were prepared by adding the vitamin solution during the rehydration procedure. In the second case a considerable decrease in entrapment values was observed but the stabilisation values remained almost the same. The close contact of the phospholipid membranes of the SUV liposomes (obtained after sonication) with the vitamin to be entrapped during the freezing and freeze drying periods appear to be a factor in the achievement of the highest entrapment values.

A further alteration in the preparation studied was the omission of the sonication step. MLV liposomes were prepared in this way and were frozen and freeze dried, while all the other conditions were maintained. A considerable decrease in entrapment values was observed followed by a slight decrease stabilisation ratio.

The form of entrapped vitamin, ie whether free or complexed, affected the entrapment values and the stabilisation ratios. Free riboflavin led to much higher entrapment values than its complexes with cyclodextrins. Betacyclodextrin complexes showed higher entrapment compared to gamma-cyclodextrin complexes. Size differentials of the complexes also affected the latency, the percentage of vitamin remaining entrapped during the suspension of the pellets in PBS. The latency can be expressed by the following equation:

$$\text{latency} = \frac{F_0 - F}{F_0} \times 100$$

where $F_0$ is the entrapped value of vitamin in pellets at time t=0 and F is the amount of released vitamin in PBS after time t.

FIG. 5 shows the latency values of various liposome preparations, ie the retention of riboflavin in the preparations in PBS. At various time intervals a known amount of the pellet suspensions were centrifuged in order to remove unentrapped riboflavin and calculations of the percentage entrapped riboflavin (latency) were made using either the supernatants or the pellets after destruction with Triton-X-100. Measurements were made in triplicate. As can be seen from FIG. 5 the release of free riboflavin from the liposomes was very fast from the MLV preparations and slower from the DRV preparations. When riboflavin was complexed with cyclodextrins the latency increased, particularly when complexed with gamma-cyclo-dextrin.

Complexes of riboflavins with cyclodextrins retained their integrity during photodegradation kinetics inside the vesicles aqueous phase implying that no interaction exist between the cyclodextrin and the other parts of the liposomes (phospholipids or cholesterol). This was determined by the fact that kinetics retained their exponential character and had the same rate constant k until all the riboflavin had degraded. If this had not been so the kinetics would be expected to have a biphasic character with slow degradation rate ($k_1$) at the start and a faster one after dissociation due to the stronger interactions of the riboflavin complex ($k_2$, $k_1<k_2$). The riboflavin complexes have stability constants, $k_c$, which indicate that they behave as if they were in aqueous solution.

From the results discussed above in Examples 5 to 10 the following conclusions were drawn: light absorbing compounds were able to provide the vitamin with only a slight increase in photostability. When the light absorbing compounds were incorporated into the lipid bilayer of liposomes so as to create a barrier to UV light increased photostability was observed (up to 4 fold). The incorporation of a variety of light absorbers into the bilayers showed even better photostability (up to 75 fold). The subsequent entrapment of water soluble light absorbers such as sulisobenzone did not further increase the photostability but decreased the entrapment values of the vitamin.

The incorporation of the antioxidant betacarotene with several lipid soluble light absorbers further increased the photostability of the vitamin. It is thought that the antioxidant was responsible for inhibiting UV radical mediated photoresponse as well as protecting the lipids of the liposome from oxidation.

Cyclodextrin inclusion complexes of riboflavin provided some increase in its photostability. When these were incorporated into the aqueous phase of the DRV liposomes and lipid soluble light absorbers and an antioxidant incorporated into the lipid bilayer a very high level of photostability was achieved, having a k value of $9.2\times10^{-5}$ $min^{-1}$. The half life of riboflavin was thus increased from 30 minutes to 5.5 days.

It is thought that the cyclodextrins have a double role in this stabilisation. They provide protection from light and also direct hydrophobic compounds in the form of complexes into the aqueous phase of the DRV liposomes. This has the advantage of separating the compound from the lipid soluble light absorbers dynamically expanding their protective effect and increasing the latency of the compounds included in the liposomes.

Thus the most dramatic increase in photostability was obtained by coentrapping a gamma-cyclodextrin inclusion complex of riboflavin with various light absorbing compounds and an antioxidant in DRV liposomes. This provided as much as a 260 fold increase in photo stability.

An of a composition described by the current invention will now be described with reference to FIG. 6. The composition comprises a liposome 1, comprising a lipid bilayer 2 membrane) and a cavity 3. The lipid bilayer is made up of lipid molecules 4, eg phospholipids (two only shown). Within the cavity 3 is located at least one material which may be photosensitive nature such as an organism or a vitamin. The material may also be present as an inclusion complex with a cyclodextrin. There is also located within the liposome 1 one or more agents capable of photostabilising the composition. Such an agent may be present within the lipid bilayer 2, within the cavity 3 or a combination of the bilayer 2 and the cavity 3. In addition, if the liposome is multilamellar (eg the membrane is formed of a plurality of bilayers) then the agent may also be located between the bilayers in one more aqueous phases, or in any combination of aqueous and lipid phases.

What is claimed is:

1. A composition comprising a liposome, the liposome retaining within its structure:

(i) an inclusion complex formed by a cyclodextrin compound and a photosensitive material, the photosensitive material undergoing photodegradation on exposure to UV light; and additionally (ii) a light-absorbing material capable of increasing the photostability of the photosensitive material in the composition, said light-absorbing material comprises one or both of an azo moiety and an aromatic moiety conjugated with a carbonyl group.

2. A composition as claimed in claim 1, further comprising an antioxidant.

3. A composition as claimed in claim 2, wherein the antioxidant is beta-carotene.

4. A composition as claimed in claim 1, wherein the light-absorbing material is selected from the group consisting of 1-[{4-[xylylazo]xylyl}-azo]-2-naphthol, 5-benzoyl-4-hydroxy-2-methoxy-benzene sulphonic acid, 2-hydroxy-4-methoxy-benzophenone and 4-methoxyphenone.

5. A composition as claimed in claim 1, wherein the light-absorbing material is associated with the liposome membrane.

6. A composition as claimed in claim 1, wherein the light-absorbing material is present within the lipid phase of the liposome membrane.

7. A composition as claimed in claim 1, wherein the light-absorbing material is associated with the hydrophilic region of the liposome membrane.

8. A composition as claimed in claim 1, wherein the liposome is a multilamellar liposome.

9. A composition as claimed in claim 1, wherein the liposome is a unilamellar liposome.

10. A composition as claimed in claim 1, wherein the liposome is a dehydration rehydration vesicle.

11. A composition as claimed in claim 1, wherein the liposome membrane comprises cholesterol.

12. A composition as claimed in claim 1, wherein the cyclodextrin compound is selected from the group consisting of β-cyclodextrin, γ-cyclodextrin, hydroxypropyl-cyclodextrin, methyl-β-cyclodextrin and polymer-β-cyclodextrin.

13. A composition as claimed in claim 1, wherein the photosensitive material is a pharmaceutically active agent or a vitamin.

14. A composition as claimed in claim 1, wherein the photosensitive material is a pharmaceutically active agent or a vitamin and wherein said photosensitive material is selected from the group consisting of riboflavin, riboflavin-5N-(dihydrogen phosphate) and a salt thereof.

15. An intimate admixture of freeze dried liposomes and a light-absorbing material comprising one or both of an azo moiety and an aromatic moiety conjugated with a carbonyl group, the intimate admixture when rehydrated in the presence of a photosensitive material forms liposomes retaining within their structures the light-absorbing material and photosensitive material, wherein the photosensitive material forms an inclusion complex formed by a cyclodextrin compound and the photosensitive material, the photosensitive material undergoing photodegradation on exposure to UV light; and further wherein the light-absorbing material increases the photostability of the photosensitive material.

16. An intimate admixture as claimed in claim 15, wherein said cyclodextrin compound is selected from the group consisting of β-cyclodextrin, γ-cyclodextrin, hydroxypropyl-cyclodextrin, methyl-β-cyclodextrin and polymer-β-cyclodextrin.

17. An intimate admixture as claimed in claim 15, wherein said light absorbing material is selected from the group consisting of 1-[{4-[xylylazo]xylyl}-azo]-2-naphthol, 5-benzoyl-4-hydroxy-2-methoxy-benzene sulphonic acid, 2-hydroxy-4-methoxy-benzophenone and 4-methoxyphenone.

18. An intimate admixture as claimed in claim 15, wherein said photosensitive material is a pharmaceutically active agent or a vitamin.

19. An intimate admixture as claimed in claim 15, wherein said photosensitive material is selected from the group consisting of riboflavin, riboflavin-5N-(dihydrogen phosphate) and a salt thereof.

20. An intimate admixture as claimed in claim 15, further comprising an antioxidant.

21. An intimate admixture as claimed in claim 15, further comprising an antioxidant wherein said antioxidant comprises beta-carotene.

22. A method of producing a composition comprising a liposome, the liposome retaining within its structure:
  (i) an inclusion complex formed by a cyclodextrin compound and a photosensitive material, the photosensitive material undergoing photodegradation on exposure to UV light; and additionally
  (ii) a light-absorbing material capable of increasing the photostability of the photosensitive material in the composition, said light-absorbing material comprises one or both of an azo moiety and an aromatic moiety conjugated with a carbonyl group,
  the method comprising the steps of:
    (a) mixing components from which the liposome is to be formed in the presence of an organic solvent;
    (b) evaporating the solvent; and
    (c) dispersing the film formed in water and isolating the liposomes so produced,
      wherein the light absorbing material is added in step (a) or step (c) or both steps (a) and (b) and the photosensitive material is added in the form of an inclusion complex in step (c).

23. A method of producing a composition, comprising a liposome, the liposome retaining within its structure;
  (i) an inclusion complex formed by a cyclodextrin compound and a photosensitive material, the photosensitive material undergoing photodegradation on exposure to UV light; and additionally
  (ii) a light-absorbing material capable of increasing the photostability of the photosensitive material in the composition, said light-absorbing material comprises one or both of an azo moiety and an aromatic moiety conjugated with a carbonyl group,
  the method comprising the following steps:
    (a) mixing components from which the liposome is to be formed in the presence of an organic solvent;
    (b) evaporating the solvent; and
    (c) dispersing the film formed in water and isolating the liposomes so produced,
      wherein the light absorbing material is added in step (a) or step (c) or steps (a) and (c) and the photosensitive material is added in the form of an inclusion complex on rehydration after further dehydration.

24. A method as claimed in either of claims 22 or 23, wherein the film is dispersed by sonication.

25. A method as claimed in either of claims 22 or 23, wherein the liposomes are freeze dried.

26. A pharmaceutical composition suitable for administration to a living organism, comprising a liposome and a physiologically acceptable carrier, the liposome retaining within its structure:
  (i) an inclusion complex formed by a cyclodextrin compound and a photosensitive material, the photosensitive material undergoing photodegradation on exposure to UV light; and
  (ii) a light-absorbing material capable of increasing the photostability of the photosensitive material in the composition, wherein said light-absorbing material comprises one or both of an azo moiety and an aromatic moiety conjugated to a carbonyl group.

27. A pharmaceutical composition according to claim 26, further comprising an antioxidant.

28. A pharmaceutical composition as claimed in claim 26, for human administration.

* * * * *